United States Patent [19]

Toda et al.

[11] Patent Number: 5,250,437

[45] Date of Patent: Oct. 5, 1993

[54] REAGENT FOR SIMULTANEOUS DETERMINATION OF HEMOGLOBIN AND LEUKOCYTES IN BLOOD

[75] Inventors: Syouzou Toda; Takashi Sakata; Yukio Hamaguchi, all of Hyogo, Japan

[73] Assignee: TOA Medical Electronics Co., Ltd., Japan

[21] Appl. No.: 596,207

[22] Filed: Oct. 10, 1990

[30] Foreign Application Priority Data

Oct. 23, 1989 [JP]  Japan .................................. 1-275280

[51] Int. Cl.$^5$ ............................................ G01N 33/48
[52] U.S. Cl. ......................................... 436/10; 436/8; 436/17; 436/18; 436/63; 436/66
[58] Field of Search .................... 436/8, 10, 11, 12, 13, 436/14, 15, 16, 17, 18, 19, 66, 71, 176, 63

[56] References Cited

U.S. PATENT DOCUMENTS

| | | | |
|---|---|---|---|
| 2,666,009 | 1/1954 | Stayner | 436/18 X |
| 4,185,964 | 1/1980 | Lancaster | 436/17 |
| 4,220,713 | 9/1980 | Rittersdorf et al. | 436/66 |
| 4,286,963 | 9/1981 | Ledis et al. | 436/63 |
| 4,290,772 | 9/1981 | Frey | 436/18 X |
| 4,297,238 | 10/1981 | Vormbrock et al. | 436/176 X |
| 4,428,908 | 1/1984 | Ashley et al. | 436/1 |
| 4,528,224 | 7/1985 | Carter et al. | 436/17 |
| 4,617,275 | 10/1986 | Matsuda et al. | 436/17 X |
| 4,745,071 | 5/1988 | Lapicola et al. | 436/17 |
| 4,793,987 | 12/1988 | Henderson et al. | 436/18 |
| 4,900,723 | 2/1990 | Schumacher | 436/69 |
| 5,116,539 | 5/1992 | Hamaguchi et al. | 436/10 X |

FOREIGN PATENT DOCUMENTS 2-31162  2/1990  Japan .

OTHER PUBLICATIONS

Clinical Biochemistry, vol. 15, No. 1, 1982, pp. 83-88, Pergamon Press, Ottawa, CA; I. Oshiro et al.: "New Method for Hemoglobin Determination By Using Sodium Lauryl Sulfate (SLS)".

*Primary Examiner*—James C. Housel
*Assistant Examiner*—Arlen Soderquist
*Attorney, Agent, or Firm*—Pearne, Gordon, McCoy & Granger

[57] ABSTRACT

A reagent for measuring the hemoglobin concentration and counting the number of leukocytes in a blood sample, which contains at least one of a quaternary ammonium salt or a pyridinium salt, having a concentration capable of hemolyzing erythrocytes in the blood and denaturing hemoglobin and at least one of cationic, nonionic or amphoteric surfactants or an oxidant capable of oxidizing heme in hemoglobin, the reagent being capable of dividing leukocytes into two or three fractions, for example, a fraction of lymphocytes, a fraction of monocytes, eosinophils and basophils, and a fraction of neutrophils.

7 Claims, 3 Drawing Sheets

REAGENT FOR SIMULTANEOUS DETERMINATION OF HEMOGLOBIN AND LEUKOCYTES IN BLOOD

BACKGROUND OF THE INVENTION

1. Field of the Invention

This invention relates to a reagent for measuring leukocytes and hemoglobin in blood samples.

2. Description of the Related Art

Measurement of hemoglobin concentration and the number of leukocytes in a blood sample is crucial for clinical diagnoses of leukemia, anemia and other hematopathys.

The basic method used for measuring or counting the number of leukocytes is a visual counting method with the aid of a microscope.

However, with the visual counting method, the erythrocytes are hemolyzed by, for example, a Türk solution, while the leukocytes are stained, and the number of the leukocytes is counted one by one on a counting plate which involves a time and labor-consuming operation.

Meanwhile, in counting the number of leukocytes in a blood sample, methods by an automatic blood analyzer are frequently employed. In counting the number of leukocytes by an automatic blood analyzer, an erythrocytolytic agent is added to the blood sample for selective hemolyzation of the erythrocytes in the blood sample to produce a sample for leukocyte measurement in which only leukocytes are left. This sample is passed through narrow paths or orifices provided in a detection section in the automatic blood analyzer, whereby electrical or optical signals are generated at the detection section, the number of these signals being a measure for the number of leukocytes.

Recently, there has also been evolved an apparatus in which, during counting of the number of leukocytes, the leukocytes are classed into granulocytes, monocytes, lymphocytes and so on depending upon the differences in their signal intensities. With the use of this automatic blood analyzer, the leukocytes can be classed and counted for more easily than with the visual counting method.

For hemoglobin measurement, on the other hand, method known as cyanmethemoglobin method is usually employed, according to which hemoglobin in the blood is converted into cyanmethemoglobin (HiCN) under the action of a hemolyzing agent containing potassium ferricyanate and cyanide and the absorbance of the cyanmethemoglobin at a specified wavelength is measured. With the automatic blood analyzer, the cyanmethemoglobin method or the method similar thereto is resorted to since the method can be used directly with the automatic blood analyzer.

However, since toxic cyanides are used with the cyanmethemoglobin method, reagent handling may endanger the operator. In addition, the waste liquor after measurement need be dumped after cyanide decomposition with the use of sodium hypochlorite, for example, by an extremely laborious operation.

For this reason, there is also employed a method, known as an oxyhemoglobin method, whereby erythrocytes are hemolyzed only with nonionic surfactants for converting hemoglobin into oxyhemoglobin (HbO$_2$), without oxidizing hemoglobin to methemoglobin, for measuring the absorbance at a predetermined wavelength. With the oxyhemoglobin method, since cyanides are not used, there is no risk in handling the reagents, while there is no necessity of performing a troublesome operation of dumping the waste liquor.

However, with the oxyhemoglobin method, a problem is raised that the blood sample with high methemoglobin contents cannot be measured accurately, since methemoglobin then may not be converted to oxyhemoglobin. As an example, Table 1 shows comparison data of the measured results obtained with the Example 1 of the present invention and the oxyhemoglobin method for the cases wherein the methemoglobin contents are changed with the use of control blood. The control blood, which is used as a substance for controlling the analytical accuracy of the automatic blood analyzer, is usually stored in a cooled state, and may exhibit a stable hemoglobin value for a prolonged time. However, on storage at higher than the ambient temperature, hemoglobin in the blood is gradually converted into methemoglobin. Therefore, when the control blood stored at 22° C. is measured by the oxyhemoglobin method, as shown in Table 1, that portion of hemoglobin which has been converted into methemoglobin becomes unable to be measured such that the measured value of hemoglobin becomes gradually lower than the initial value in several days.

As a solution to this problem, a reagent for hemoglobin measurement comprised of dodecyl sodium sulfate or equal amounts of lauryl sodium sulfate (SLS) (an anionic surfactant), and Triton X-100 (a nonionic surfactant), in a neutral buffer (pH, 7.2), is taught by Ōshiro et al in Clinical Biochemistry, vol. 15, 83 (1982).

With this method, the hemoglobin concentration in the blood may be measured without being affected by methemoglobin, while there is no necessity of treating the waste liquor because of the absence of cyanide contents.

However, it is not possible with this method to measure leukocytes simultaneously with hemoglobin measurement.

The Japanese Patent Public Disclosure (KOKAI) No. 61-148369 (1986) entitled "CYANIDE-FREE HEMOGLOBIN REAGENT" discloses a reagent for hemoglobin measurement with the aid of an ionic surfactant. However, it is similarly not possible with this reagent to measure the leukocytes simultaneously with the hemoglobin.

As discussed hereinabove, it is not possible with the prior-art technology to measure hemoglobin and leukocytes simultaneously by a cyanide-free reagent or to make a correct measurement of hemoglobin in a blood sample with high methemoglobin contents.

SUMMARY OF THE INVENTION

As a result of perseverant researches, the present inventors have arrived at the following reagent for solution of the above-mentioned problems of the prior art.

In accordance with the present invention, there is provided a reagent for measuring the hemoglobin concentration and counting the number of leukocytes in a blood sample, which reagent satisfies the following conditions:

i) It contains at least one of a quaternary ammonium salt (formula a) or a pyridinium salt (formula b), having a concentration capable of hemolyzing erythrocytes in the blood and denaturing hemoglobin:

$$\left[ \begin{array}{c} R_2 \\ | \\ R_1-N^+-R_3 \\ | \\ R_4 \end{array} \right] X^-$$  formula a where $R_1$: $C_8$ to $C_{20}$ alkyl, alkenyl or alkynyl group;
$R_2$, $R_3$ and $R_4$: $C_1$ to $C_8$ alkyl, alkenyl or alkynyl group; and
$X^-$: anionic group;

$$\left[ \bigotimes N^+-(CH_2)_n-CH_3 \right] X^-$$  formula b where n: an integer of from 7 to 19; and
$X^-$: an anionic group.

ii) The reagent contains at least one compound selected from the group consisting of cationic, nonionic or amphoteric surfactants as shown by the formulas c to e and an oxidant capable of oxidizing heme in hemoglobin as shown by the formula f:

$$\left[ \begin{array}{c} R_2 \\ | \\ R_1-N^+-CH_2-\bigotimes \\ | \\ R_3 \end{array} \right] X^-$$  formula c where $R_1$: $C_8$ to $C_{20}$ alkyl, alkenyl or alkynyl group;
$R_2$ and $R_3$: $C_1$ to $C_8$ alkyl, alkenyl or alkynyl group; and
$X^-$: anionic group;

$R_1-R_2-(CH_2CH_2O)_n-H$  formula d where $R_1$: $C_8$ to $C_{20}$ alkyl, alkenyl or alkynyl group;

$R_2$: O, $\bigotimes$—O— or COO; and n: an integer of from 10 to 50;

$$\begin{array}{c} R_2 \\ | \\ R_1-N^+-CH_2COO^- \\ | \\ R_3 \end{array}$$  formula e where $R_1$: $C_8$ to $C_{20}$ alkyl group; and
$R_2$ and $R_3$: $C_1$ to $C_8$ alkyl, alkenyl or alkinyl group;
formula f. nitrite ion, quinone compound, alloxan, methylene blue, aniline, acetanilide, nitrobenzene, acetophenetidin, nitrotoluene, sulfonamide, phenylhydrazine, ascorbic acid or aminophenol.

iii) The reagent is a solution with a pH ranging from 3.0 to 9.0.
iv) The total concentration of the quaternary ammonium salt is in the range of from 0.1 to 15.0 g/l.
v) The total concentration of the pyridinium salt is in the range of from 0.1 to 15.0 g/l.
vi) The total concentration of the oxidant is in the range of from 0.5 to 10.0 g/l.
vii) The total concentration of the nonionic surfactant is in the range of from 0.1 to 15.0 g/l.
viii) The total concentration of the amphoteric surfactant is in the range of from 0.1 to 15.0 g/l.
ix) The total concentration of the cationic surfactant is in the range of from 0.1 to 15.0 g/l.

By suitably combining the components of formulas a to f in the above reagent, leukocytes may be divided into two or three fractions, for example, a fraction of lymphocytes, a fraction of monocytes, eosinophils and basophils, and a fraction of neutrophils.

DESCRIPTION OF THE PREFERRED EMBODIMENTS

Figure 1:
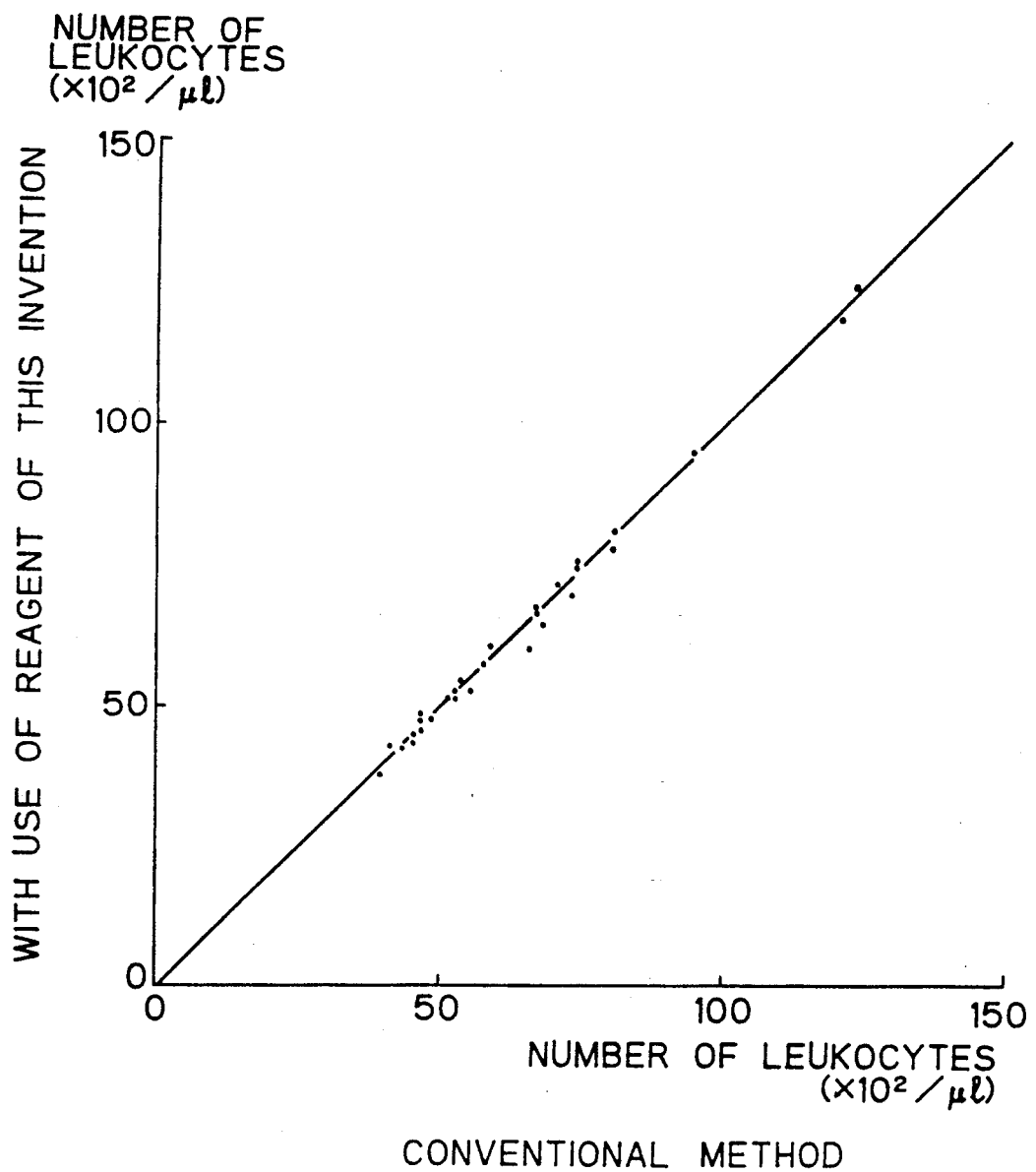
FIG. 1 is a graph of leukocyte count obtained by the conventional method plotted against that obtained by the method of the invention.

The following are the compositional examples of the reagent of the present invention.

| | Concentration Range |
|---|---|
| Compositional Example 1 | |
| myristyltrimethylammonium bromide (quaternary ammonium salt) | 0.2 to 5.0 g |
| sodium nitrite | 0.5 to 10.0 g |
| phosphate buffer | 1/15 to 1/60M |
| sodium chloride | 1.0 to 10.0 g |
| distilled water | 1 l |
| Compositional Example 2 | |
| myristyltrimethylammonium bromide | 0.2 to 5.0 g |
| polyoxyethylene nonylphenylether (nonionic surfactant) | 0.1 to 10.0 g |
| sodium nitrite | 0.5 to 10.0 g |
| phosphate buffer | 1/15 to 1/60M |
| sodium chloride | 1.0 to 10.0 g |
| distilled water | 1 l |
| Compositional Example 3 | |
| lauryltrimethylammonium chloride (quaternary ammonium salt) | 0.3 to 10.0 g |
| cetyltrimethylammonium chloride (quaternary ammonium salt) | 0.01 to 2.0 g |
| sodium nitrite | 0.5 to 10.0 g |
| phosphate buffer | 1/15 to 1/60M |
| sodium chloride | 1.0 to 10.0 g |
| distilled water | 1 l |

In the Compositional Examples 1 to 3, erythrocytes are hemolyzed in a quaternary ammonium salt or salts, while hemoglobin is denatured and added to by sodium nitrite as an oxidizing agent for heme in order to accelerate the denaturation and to stabilize hemoglobin.

In the Compositional Example 2, the leukocytes may be divided into two fractions by the addition of the nonionic surfactant and, in the Compositional Example 3, the leukocytes may be divided into two or more fractions by combining two different quaternary ammonium salts.

The term "total concentration of the quaternary ammonium salt or salts" as used in the claim means the concentration of lauryltrimethylammonium chloride and the concentration of cetyltrimethylammonium chloride summed together, ranging from 0.31 to 12.0 g.

|  | Concentration Range |
|---|---|
| Compositional Example 4 | |
| lauryltrimethylammonium chloride | 0.5 to 10.0 g |
| lauryldimethylaminoacetic acid betaine (amphoteric surfactant) | 0.5 to 10.0 g |
| phosphate buffer | 1/15 to 1/60M |
| sodium chloride | 1.0 to 10.0 g |
| distilled water | 1 l |
| Compositional Example 5 | |
| lauryltrimethylammonium chloride | 1.0 to 10.0 g |
| polyoxyethylene nonylphenylether | 1.0 to 10.0 g |
| phosphate buffer | 1/15 to 1/60M |
| sodium chloride | 1.0 to 10.0 g |
| distilled water | 1 l |
| Compositional Example 6 | |
| lauryltrimethylammonium chloride | 3.0 to 10.0 g |
| laurylbenzylammonium chloride (cationic surfactant) | 3.0 to 10.0 g |
| phosphate buffer | 1/15 to 1/60M |
| sodium chloride | 1.0 to 10.0 g |
| distilled water | 1 l |
| Compositional Example 7 | |
| laurylpyridinium chloride (pyridinium salt) | 0.5 to 10.0 g |
| lauryldimethlaminoacetic acid betaine | 0.5 to 10.0 g |
| phosphate buffer | 1/15 to 1/20M |
| sodium chloride | 1.0 to 10.0 g |
| distilled water | 1 l |

In the Compositional Examples 4 to 7, the combination of the quaternary ammonium salt and the amphoteric surfactant, the combination of the quaternary ammonium salt and the nonionic surfactant, the combination of the quaternary ammonium salt and the cationic surfactant and the combination of the pyridinium salt and the amphoteric surfactant are used, respectively, for denaturing and stabilizing hemoglobin.

It is noted that, by adjusting the concentration of each of the ingredients, leukocytes can be divided into two or more fractions.

In the Compositional Examples 1 to 7, the phosphate buffer is used for adjusting the pH of the solution to from 3.0 to 9.0. Thus, there is, however, no limitation on the types of buffers, and any buffer other than a phosphate buffer, such as citrate buffer, maleate buffer or tris buffer, may be employed. The preferred pH range is from 5.0 to 8.0. If the pH is lower than 3.0, damages to leukocytes are increased to render the measurement of leukocytes difficult. If the pH is higher than 9.0, chronological stability of hemoglobin deteriorates. Sodium chloride is used for adjusting the electrical conductivity of the solution to a level that may be measured with an automatic blood analyzer.

The concentration of each of the ingredients defined in the claim means the concentration in the state in which measurement may be made only upon addition of the blood into the reagent and without the necessity of using other diluents. However, with the use of a conventional apparatus in which the diluents and the reagent for hemolyzation are mixed together at a predetermined ratio for measuring hemoglobin and leukocytes, the concentration of each of the ingredients such as surfactants may be changed as a function of the mixing ratios for the apparatus, in which case the concentration of each of the ingredients defined in the claim stands for the concentration in the liquid mixture containing the diluents and the reagent for hemolyzation.

According to the present invention,
i) both hemoglobin and leukocytes can be measured by one reagent;
ii) even a blood sample with a high content of methemoglobin contents can be measured; and
iii) since the reagent is free of cyanides, the troublesome operation of removing it from the waste liquor may be eliminated.

In addition, when the reagent is used in an automatic blood analyzer, it becomes unnecessary to provide the hemoglobin measurement unit and the leukocyte measurement unit separately, or to provide two separate series of the fluid system, so that the apparatus may be simplified in structure and the cost thereof lowered.

DETAILED DESCRIPTION OF THE DRAWINGS

Figure 2:
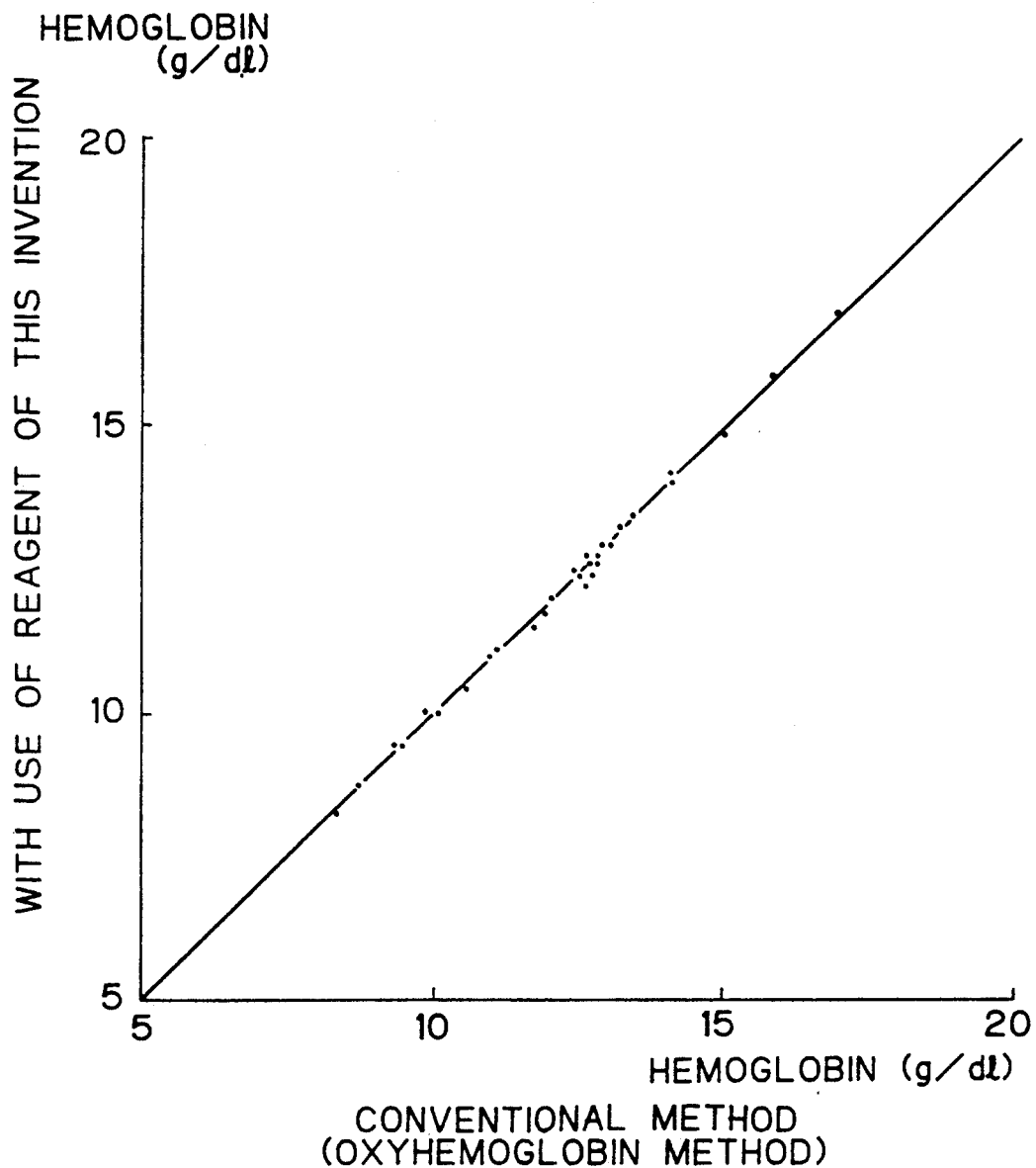
FIG. 2 is a graph of hemoglobin concentration obtained by the conventional method plotted against that obtained by the method of the invention.
Figure 3:
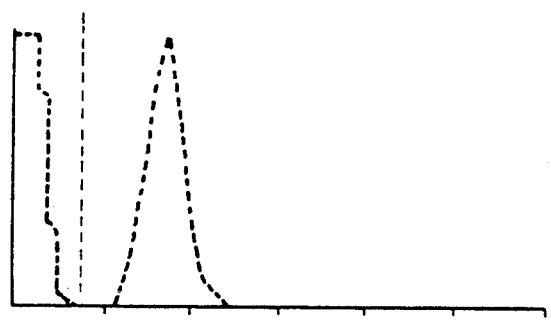
FIGS. 3, 4, and 5 are plots of relative frequency plotted against relative intensity of leukocyte particle size distribution with the use of reagents of Examples 1, 2, and 3, respectively.
Figure 4:
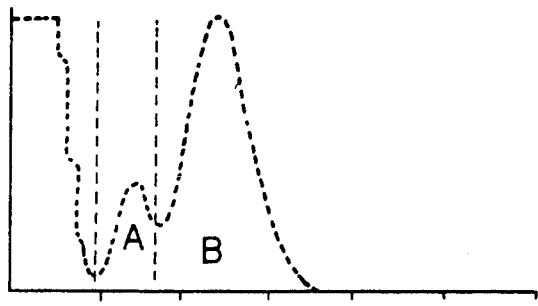
Figure 5:
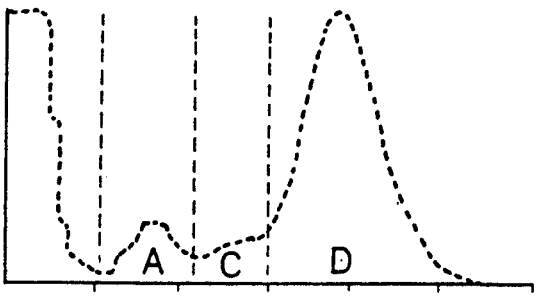

FIG. 1 is a chart showing the correlation between the results of measurement of the number of leukocytes by the conventional method using an apparatus E-4000 manufactured by Toa Medical Electronics Co., Ltd. and those with the use of the reagent of Example 1;

FIG. 2 is a chart showing the correlation between the results of measurement of the hemoglobin value by the conventional oxyhemoglobin method and those with the use of the reagent of Example 1; and FIGS. 3 to 5 are charts showing leukocyte particle size distribution with the use of the reagents of Examples 1 to 3, respectively.

EXAMPLES

The present invention will be explained in more detail with reference to the following Examples which are given only for the sake of illustration and are not intended to limit the scope of the invention.

EXAMPLE 1

|  | Concentration |
|---|---|
| myristyltrimethylammonium bromide | 0.7 g |
| sodium nitrite | 1.4 g |
| phosphate buffer | 1/25M (pH 6) |
| sodium chloride | q.s. (adjusted to electrical conductivity close to 13 ms/cm) |
| distilled water | 1 l |

FIG. 1 shows the correlation between the results of measurement of the number of leukocytes by the conventional method employing the E-4000 type apparatus manufactured by Toa Medical Electronics Co., Ltd. and results of measurement with the reagent of the Example 1. The correlation coefficient r=0.996 and the regression line y=1.013x−0.673, thus indicating an extremely high correlation.

FIG. 2 shows the correlation between the results of measurement of the hemoglobin value by the conventional oxyhemoglobin method and results of measurement with the reagent of Example 1. The correlation coefficient r=0.999 and the regression line y=1.004x−0.027, thus indicating an extremely high correlation.

Even when the measured value of hemoglobin by the oxyhemoglobin method decreases due to an increase in the quantity of methemoglobin as shown in Table 1, the value of hemoglobin as measured with the reagent of Example 1 is not changed but remains constant.

Meanwhile, the difference between the initial value given by the oxyhemoglobin method as shown in Table 1 and the initial value given by the reagent of Example 1 may be attributed to the use of a control blood in which a predetermined quantity of hemoglobin in the blood has been converted from the outset into methemoglobin.

TABLE 1

Results of Measurement of Control Blood
(Oxyhemoglobin Method vs Example 1)

|  | Oxyhemoglobin Method | Measurement by reagent of Example 1 |
|---|---|---|
| initial value | 17.0 g/l | 18.1 g/l |
| on storage at 22° C. for 3 days | 16.5 g/l | 18.1 g/l |
| on storage at 22° C. for 7 days | 16.0 g/l | 18.1 g/l |

EXAMPLE 2

The reagent of the following composition was prepared.

|  | Concentration |
|---|---|
| lauryltrimethylammonium chloride | 1.5 g |
| cetyltrimethylammonium chloride | 0.4 g |
| sodium nitrite | 1.4 g |
| phosphate buffer | 1/25M (pH 6) |
| sodium chloride | q.s. (adjusted to electrical conductivity close to 13 sm/cm) |
| distilled water | 1 l |

EXAMPLE 3

The reagent of the following composition was prepared.

|  | Concentration |
|---|---|
| lauryltrimethylammonium chloride | 3.2 g |
| cetyltrimethylammonium chloride | 0.2 g |
| sodium nitrite | 1.4 g |
| phosphate buffer | 1/25M (pH 6) |
| sodium chloride | q.s. (adjusted to electrical conductivity close to 13 ms/cm) |
| distilled water | 1 l |

FIGS. 3 to 5 show the leukocyte particle size distribution with the use of the reagents of the Examples 1 to 3, respectively. In these figures, the ordinate stands for the relative intensity of the blood cell signals, that is the size of the blood cells, that is obtained upon measurement of the blood cells with the aid of the automatic blood analyzer. Thus, with the use of the reagent of Example 1, the leukocytes indicate a single-peak particle size distribution, as shown in FIG. 3. With the use of the reagent of the Example 2, the leukocytes indicate a particle size distribution divided into a region A for an aggregate of lymphocytes and a region B for an aggregate of leukocytes other than lymphocytes, as shown in FIG. 4. With the use of the reagent of Example 3, the leukocytes indicate a particle size distribution divided into a region A for an aggregate of lymphocytes, a region C for an aggregate of monocytes, eosinophils and basophils, and a region D for an aggregate of neutrophils, as shown in FIG. 5.

It will be seen from the foregoing that, with the use of the reagent of the present invention, not only the measured results similar to those given by the conventional practice may be obtained, but i) hemoglobin and leukocytes may be measured simultaneously, while leukocytes may be divided into fractions;

ii) since the reagent is free of cyanide or similar toxic substances, disposal of waste liquor can be easily effected without danger to the environment; and iii) a blood sample with high methemoglobin contents may be measured correctly.

In addition, the measurement apparatus may be simplified in structure and lowered in costs.

What is claimed is:

1. A reagent for enabling measuring a hemoglobin concentration by counting the number of leukocytes present in a blood sample to be counted, which is free of cyanides comprising a solution with a pH ranging from 3.0 to 9.0 containing:

(i) at least two quaternary ammonium salts having the formula:

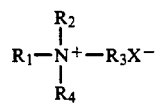

where $R_1$ is a $C_8$ to $C_{20}$ alkyl, alkenyl or alkynyl group, $R_2$, $R_3$, and $R_4$ are a $C_1$ to $C_8$ alkyl, alkenyl or alkynyl group, $X^-$ is an anionic group;

said quaternary ammonium salts having a total concentration in the range of 0.1 to 12.0 g/l and being capable of hemolyzing the erythrocytes in the blood and denaturing hemoglobin; and ii) at least one oxidant capable of oxidizing heme in hemoglobin, selected from the group consisting of nitrite ion, quinone, alloxan, methylene blue, aniline, acetanilide, nitrobenzene, acetophenetidin, nitrotoluene, sulfonamide, phenylhydrazine, ascorbic acid and aminophenol; said at least one oxidant having a total concentration in the range of 0.5 to 10.0 g/l, and said reagent is capable of dividing leukocytes into at least two fractions.

2. A reagent as claimed in claim 1, wherein said quaternary ammonium salts have a total concentration in the range of 2.2 to 5.0 g/l, and said reagent is capable of dividing leukocytes into three fractions.

3. A reagent for enabling measuring a hemoglobin concentration by counting the number of leukocytes present in a blood sample to be counted, which is free of cyanides comprising a solution with a pH ranging from 3.0 to 9.0 containing:

(i) at least one quaternary ammonium salt having the formula:

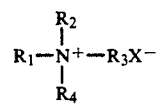

where $R_1$ is a $C_8$ to $C_{20}$ alkyl, alkenyl or alkynyl group, $R_2$, $R_3$, and $R_4$ are a $C_1$ to $C_8$ alkyl, alkenyl or alkynyl group, $X^-$ is an anionic group;

said quaternary ammonium salts having a total concentration in the range of 0.1 to 12.0 g/l and being capable of hemolyzing erythrocytes in the blood and denaturing hemoglobin; and ii) at least one nonionic surfactant having the formula:

$$R_1-R_2-(CH_2CH_2O)_n-H$$

where $R_1$ is a $C_8$ to $C_{20}$ alkyl, alkenyl or alkynyl group,

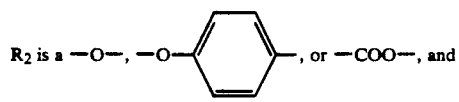

$R_2$ is a $-O-$, $-O-\phantom{x}$, or $-COO-$, and n is an integer of from 10 to 50; said at least one nonionic surfactant having a total concentration in the range of 0.1 to 12.0 g/l, and iii) at least one oxidant capable of oxidizing heme in hemoglobin, selected from the group consisting of nitrite, ion, quinone, alloxan, methylene blue, aniline, acetanilide, nitrobenzene, acetophenetidin, nitrotoluene, sulfonamide, phenylhydrazine, ascorbic acid and aminophenol; said at least one oxidant having a total concentration in the range of 0.5 to 10.0 g/l, and said reagent is capable of dividing leukocytes into at least two fractions.

4. A reagent for enabling measuring a hemoglobin concentration by counting the number of leukocytes present in a blood sample to be counted, which is free of cyanides comprising a solution with a pH ranging from 3.0 to 9.0 containing:

i) at least one quaternary ammonium salt having the formula:

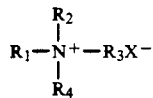

where $R_1$ is a $C_8$ to $C_{20}$ alkyl, alkenyl or alkynyl group, $R_2$, $R_3$, and $R_4$ are a $C_1$ to $C_8$ alkyl, alkenyl or alkynyl group, $X^-$ is an anionic group;

said quaternary ammonium salts having a total concentration in the range of 0.1 to 12.0 g/l and being capable of hemolyzing erythrocytes in the blood and denaturing hemoglobin; and ii) at least one amphoteric surfactant having the formula:

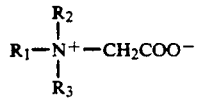

where $R_1$ is a $C_8$ to $C_{20}$ alkyl group, $R_2$ and $R_3$ are a $C_1$ to $C_8$ alkyl, alkenyl or alkynyl group, said at least one amphoteric surfactant having a total concentration in the range of 0.1 to 12.0 g/l, and said reagent is capable of dividing leukocytes into at least two fractions.

5. A reagent as claimed in claim 4, wherein said amphoteric surfactant or surfactants have a total concentration in the range of 0.1 to 10.0 g/l, and said reagent is capable of dividing leukocytes into three fractions.

6. A reagent for enabling measuring a hemoglobin concentration by counting the number of leukocytes present in a blood sample to be counted, which is free of cyanides comprising a solution with a pH ranging from 3.0 to 9.0 containing:

i) at least one quaternary ammonium salt having the formula:

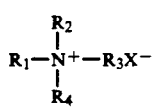

where $R_1$ is a $C_8$ to $C_{20}$ alkyl, alkenyl or alkynyl group, $R_2$, $R_3$, and $R_4$ are a $C_1$ to $C_8$ alkyl, alkenyl or alkynyl group, $X^-$ is an anionic group;

said quaternary ammonium salts having a total concentration in the range of 0.1 to 12.0 g/l and being capable of hemolyzing erythrocytes in the blood and denaturing hemoglobin; and ii) at least one cationic surfactant having the formula:

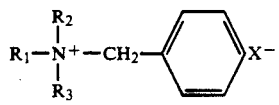

where $R_1$ is a $C_8$ to $C_{20}$ alkyl, alkenyl or alkynyl group, $R_2$ and $R_3$ are a $C_1$ to $C_8$ alkyl, alkenyl or alkynyl group, $X^-$ is an anionic group;

said at least one cationic surfactant having a total concentration in the range of 0.1 to 5.0 g/l, and said reagent is capable of dividing leukocytes into at least two fractions.

7. A reagent for enabling measuring a hemoglobin concentration by counting the number of leukocytes present in a blood sample to be counted, which is free of cyanides comprising a solution with a pH ranging from 3.0 to 9.0 containing:

(i) at least two quaternary ammonium salts having the formula:

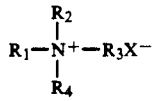

where $R_1$ is a $C_8$ to $C_{20}$ alkyl, or alkynyl group, $R_2$, $R_3$, and $R_4$ are a $C_1$ to $C_8$ alkyl, alkenyl or alkynyl group, $X^-$ is an anionic group;

said quaternary ammonium salts having a total concentration in the range of 1.0 to 10.0 g/l and being capable of hemolyzing erythrocytes in the blood and denaturing hemoglobin; and (ii) at least one pyridinium salt, having the formula:
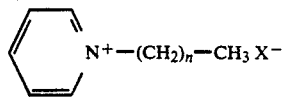
where n is an integer of from 7 to 19, and
X$^-$ is an anionic group,
the total concentration of pyridinium salts is in the range of 1.0 to 5.0 g/l, and said agent is capable of dividing leukocytes into three fractions.
* * * * *

UNITED STATES PATENT AND TRADEMARK OFFICE
CERTIFICATE OF CORRECTION

PATENT NO. : 5,250,437  
DATED : October 5, 1993  
INVENTOR(S) : Toda et al.

It is certified that error appears in the above-indentified patent and that said Letters Patent is hereby corrected as shown below:

Column 6, after the centered heading "EXAMPLE 1" the following sentence should be inserted:

--The reagent of the following composition was prepared.--

Column 6, line 48, in Example 1, delete "13 ms/cm" and insert --13 mS/cm--.

Column 7, line 34, in Example 2, delete "13 sm/cm" and insert --13 mS/cm--.

Column 7, line 48, in Example 3, delete "13 sm/cm" and insert --13 mS/cm--.

Column 8, line 19, (Claim 1, line 2), delete "by" and insert --and--.

Column 8, line 55, (Claim 3, line 2), delete "by" and insert --and--.

UNITED STATES PATENT AND TRADEMARK OFFICE
CERTIFICATE OF CORRECTION

PATENT NO. : 5,250,437
DATED : October 5, 1993
INVENTOR(S) : Toda et al.

Page 2 of 2

It is certified that error appears in the above-indentified patent and that said Letters Patent is hereby corrected as shown below:

Column 9, line 35, (Claim 4, line 2), delete "by" and insert --and--.

Column 10, line 8, (Claim 6, line 2), delete "by" and insert --and--.

Column 10, line 48, (Claim 7, line 2), delete "by" and insert --and--.

Signed and Sealed this

Thirty-first Day of October 1995

Attest:

BRUCE LEHMAN

*Attesting Officer*  *Commissioner of Patents and Trademarks*